United States Patent [19]

Andree et al.

[11] Patent Number: 5,496,793
[45] Date of Patent: Mar. 5, 1996

[54] SUBSTITUTED CARBAMOYLTRIAZOLES

[75] Inventors: Roland Andree, Langenfeld; Markus Dollinger; Hans-Joachim Santel, both of Leverkusen, all of Germany

[73] Assignee: Bayer Aktiengesellschaft, Leverkusen, Germany

[21] Appl. No.: 340,513

[22] Filed: Nov. 16, 1994

[30] Foreign Application Priority Data

Nov. 23, 1993 [DE] Germany .......................... 43 39 863.4

[51] Int. Cl.$^6$ ...................... A01N 43/653; C07D 249/12
[52] U.S. Cl. ...................... 504/273; 548/264.4; 546/210; 540/603; 504/210; 504/219
[58] Field of Search ................ 548/264.4; 546/210; 540/603; 504/210, 219, 273

[56] References Cited

FOREIGN PATENT DOCUMENTS 0332133  9/1989  European Pat. Off. .

*Primary Examiner*—Patricia L. Morris
*Attorney, Agent, or Firm*—Sprung Horn Kramer & Woods

[57] ABSTRACT

The invention relates to new substituted carbamoyltriazoles of the general formula (I)

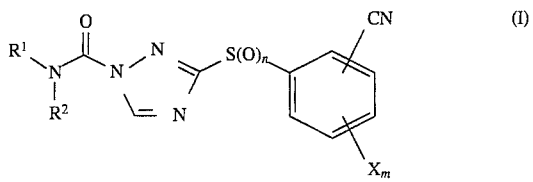

in which m represents the numbers 0 to 4, n represents the numbers 0, 1 or 2, $R^1$ represents a radical from the series comprising alkyl, alkenyl or alkinyl, each of which is optionally substituted, $R^2$ represents a radical from the series comprising alkyl, alkenyl or alkinyl, each of which is optionally substituted, or together with $R^1$ represents alkanediyl, and X represents halogen, hydroxyl, amino, mercapto, or represents a radical from the series comprising alkyl, alkoxy, alkylthio, alkylamino, alkanoylamino, alkylsulphonylamino, cycloalkyloxy, cycloalkylthio, cycloalkylamino, cycloalkylalkoxy, cycloalkylalkylthio, cycloalkylalkylamino, aryloxy, arylthio, arylamino, arylcarbonyl, arylsulphonyl, arylalkyl, arylalkoxy, arylalkylthio, arylalkylamino, arylalkylcarbonyl or arylalkylsulphonyl, each of which is optionally substituted, to a process for their preparation and to their use as herbicides, and to novel intermediates.

7 Claims, No Drawings

SUBSTITUTED CARBAMOYLTRIAZOLES

The invention relates to new substituted carbamoyltriazoles, to a process for their preparation and to their use as herbicides, and to novel intermediates.

It has already been disclosed that certain substituted carbamoyltriazoles, such as, for example, the compound 1-(diethylaminocarbonyl)-3-(2,4,6-trimethylphenylsulphonyl)-1,2,4-triazole, have herbicidal properties (cf. EP-A-332133).

However, the herbicidal activity or the tolerance of these known compounds by crop plants is not always entirely satisfactory.

The novel substituted carbamoyltriazoles of the general formula (I) have now been found,

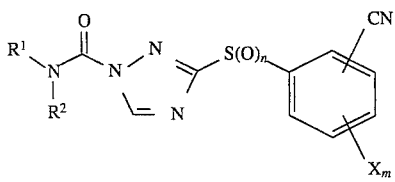

(I)

in which
  m represents the numbers 0 to 4,
  n represents the numbers 0, 1 or 2,
  $R^1$ represents a radical from the series comprising alkyl, alkenyl or alkinyl, each of which is optionally substituted,
  $R^2$ represents a radical from the series comprising alkyl, alkenyl or alkinyl, each of which is optionally substituted, or together with $R^1$ represents alkanediyl, and
  X represents halogen, hydroxyl, amino, mercapto, or represents a radical from the series comprising alkyl, alkoxy, alkylthio, alkylamino, alkanoylamino, alkylsulphonylamino, cycloalkyloxy, cycloalkylthio, cycloalkylamino, cycloalkylalkoxy, cycloalkylalkylthio, cycloalkylalkylamino, aryloxy, arylthio, arylamino, arylcarbonyl, arylsulphonyl, arylalkyl, arylalkoxy, arylalkylthio, arylalkylamino, arylalkylcarbonyl or arylalkylsulphonyl, each of which is optionally substituted.

The novel substituted carbamoyltriazoles of the general formula (I) are obtained when carbamoyl chlorides of the general formula (II)

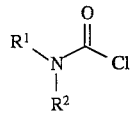

(II)

in which
$R^1$ and $R^2$ have the abovementioned meanings
are reacted with substituted triazoles of the general formula (III)

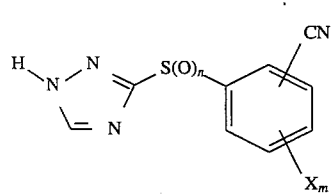

(III)

in which
m, n and X have the abovementioned meanings,
if appropriate in the presence of an acid acceptor and, if appropriate, in the presence of a diluent,
the resulting compounds of the formula (I) in which n represents 0 are, if appropriate, converted by reacting them with an oxidant to give corresponding compounds of the formula (I) in which n represents 1 or 2, and/or the resulting compounds of the formula (I) in which X represents halogen are, if appropriate, converted by reacting them with compounds of the formula (IV)

$$MX^1 \qquad (IV)$$

in which
  M represents hydrogen or a metal equivalent and
  $X^1$ has the meaning given above for X with the exception of halogen and alkyl,
to give correspondingly derivatized compounds of the formula (I).

The new substituted carbamoyltriazoles of the general formula (I) are distinguished by a powerful and selective herbicidal activity.

Surprisingly, the compounds of the formula (I) according to the invention show a considerably more powerful and better selective herbicidal activity than the compounds which are known from the prior art and which have a similar structure and the same direction of action, such as, for example, the compound 1-(diethylaminocarbonyl)-3-(2,4,6-trimethylphenylsulphonyl)-1,2,4-triazole.

The invention preferably relates to the compounds of the formula (I) in which
  m represents the numbers 0, 1, 2, 3 or 4,
  n represents the numbers 0, 1 or 2,
  $R^1$ represents a radical from the series comprising alkyl, alkenyl or alkinyl, each of which has up to 6 carbon atoms and each of which is optionally substituted by halogen,
  $R^2$ represents a radical from the series comprising alkyl, alkenyl or alkinyl, each of which has up to 6 carbon atoms and each of which is optionally substituted by halogen, or together with $R^1$ represents alkanediyl having 2 to 6 carbon atoms, and
  X represents halogen, hydroxyl, amino, mercapto,
  X furthermore represents a radical from the series comprising alkyl, alkoxy, alkylthio, alkylamino, alkanoylamino or alkylsulphonylamino, each of which has up to 6 carbon atoms in the alkyl groups and each of which is optionally substituted by halogen, cyano, hydroxyl, carboxyl, $C_1$–$C_4$-alkoxy, $C_1$–$C_4$-alkyl-carbonyl or $C_1$–$C_4$-alkoxy-carbonyl,
  X furthermore represents a radical from the series comprising cycloalkyloxy, cycloalkylthio, cycloalkylamino, cycloalkylalkoxy, cycloalkyl-alkylthio or cycloalkyl-alkylamino, each of which has 3 to 6 carbon atoms in the cycloalkyl groups and, if appropriate, 1 to 4 carbon atoms in the alkyl groups and each of which is optionally substituted by halogen, cyano, carboxyl, $C_1$–$C_4$-alkyl or $C_1$–$C_4$-alkoxy-carbonyl, or
  X furthermore represents a radical from the series comprising aryloxy, arylthio, arylamino, arylcarbonyl, arylsulphonyl, arylalkyl, arylalkoxy, arylalkylthio, arylalkylamino, arylalkylcarbonyl or arylalkylsulphonyl, each of which has 6 or 10 carbon atoms in the aryl groups and, if appropriate, 1 to 4 carbon atoms in the alkyl groups, and each of which is optionally substituted by halogen, cyano, nitro, hydroxyl, amino, carboxyl, $C_1$–$C_4$-alkyl, $C_1$–$C_4$-halogenoalkyl, $C_1$–$C_4$-alkoxy, $C_1$–$C_4$-halogenoalkoxy, $C_1$–$C_4$-alkylthio, $C_1$–$C_4$-halogenoalkylthio, $C_1$–$C_4$-alkylsulphinyl, $C_1$–$C_4$-halogenoalkylsulphinyl, $C_1$–$C_4$-alkylsulphonyl, $C_1$–$C_4$-halogenoalkylsulphonyl or $C_1$–$C_4$-alkoxycarbonyl.

The hydrocarbon radicals which have been mentioned in the definitions of the radicals, such as alkyl, alkenyl or alkinyl, also in combination with hetero atoms, such as in alkoxy, alkylthio or alkylamino, are straight-chain or branched, even when this is not mentioned expressly.

Halogen generally represents fluorine, chlorine, bromine or iodine, preferably fluorine, chlorine or bromine, in particular fluorine or chlorine.

In particular, the invention relates to compounds of the formula (I) in which m represents the numbers 0, 1, 2, 3 or 4, n represents the numbers 0, 1 or 2, $R^1$ represents a radical from the series comprising methyl, ethyl, n- or i-propyl, n-, i- or s-butyl, propenyl, butenyl, propinyl or butinyl, each of which is optionally substituted by fluorine, $R^2$ represents a radical from the series comprising methyl, ethyl, n- or i-propyl, n-, i- or s-butyl, propenyl, butenyl, propinyl or butinyl, each of which is optionally substituted by fluorine, or together with $R^1$ represents ethane-1,2-diyl (dimethylene), propane-1,3-diyl (trimethylene) or butane-1,4-diyl (tetramethylene) and X represents fluorine, chlorine, bromine, hydroxyl, amino, mercapto, X furthermore represents a radical from the series comprising methyl, ethyl, n- or i-propyl, n-, i-, s-, or t-butyl, methoxy, ethoxy, n- or i-propoxy, n-, i-, s- or t-butoxy, methylthio, ethylthio, n- or i-propylthio, n-, s-, i- or t-butylthio, methylamino, ethylamino, n- or i-propylamino, n-, i-, s- or t-butylamino, acetylamino, propionylaraino, butyroylamino, methylsulphonylamino, ethylsulphonylamino, n- or i-propylsulphonylamino, n-, i-, s- or t-butylsulphonylamino, each of which is optionally substituted by fluorine, chlorine, bromine, cyano, hydroxyl, carboxyl, methoxy, ethoxy, methoxycarbonyl or ethoxycarbonyl, X furthermore represents a radical from the series comprising cyclopentyloxy, cyclohexyloxy, cyclopentylthio, cyclohexylthio, cyclopentylamino, cyclohexylamino, cyclopentylmethoxy, cyclohexylmethoxy, cyclopentyl-methylthio, cyclohexylmethylthio, cyclopentylmethylamino, or cyclohexylmethylamino, each of which is optionally substituted by fluorine, chlorine, bromine, cyano, carboxyl, methyl, ethyl, n- or i-propyl, methoxycarbonyl or ethoxycarbonyl, or X furthermore represents a radical from the series comprising phenoxy, phenylthio, phenylamino, phenylcarbonyl, phenylsulphonyl, benzyl, benzyloxy, benzylthio, benzylamino, phenylacetyl or benzylsulphonyl, each of which is optionally substituted by fluorine, chlorine, bromine, cyano, nitro, hydroxyl, amino, carboxyl, methyl, ethyl, trifluoromethyl, methoxy, ethoxy, difluoromethoxy, trifluoromethoxy, methylthio, ethylthio, difluoromethylthio, trifluoromethylthio, methylsulphinyl, ethylsulphinyl, methylsulphonyl, ethylsulphonyl, trifluoromethylsulphonyl, methoxycarbonyl or ethoxycarbonyl.

The abovementioned general definitions of radicals or those whose preferred ranges have been given apply to the end products of the formula (I) and, analogously, to the starting substances or intermediates required in each case for their preparation.

These definitions of radicals can be combined with each other as desired, that is to say combinations between the stated ranges of preferred compounds are also possible.

If, for example, diethylcarbamoyl chloride and 3-(2-chloro-4-cyano-5-fluoro-phenylthio)-1H-1,2,4-triazole are used as starting substances, hydrogen peroxide as an oxidant for a subsequent oxidation reaction and methyl hydroxyacetate as reactant for a subsequent substitution reaction, the course of the reaction in the process according to the invention can be outlined by the following equation:

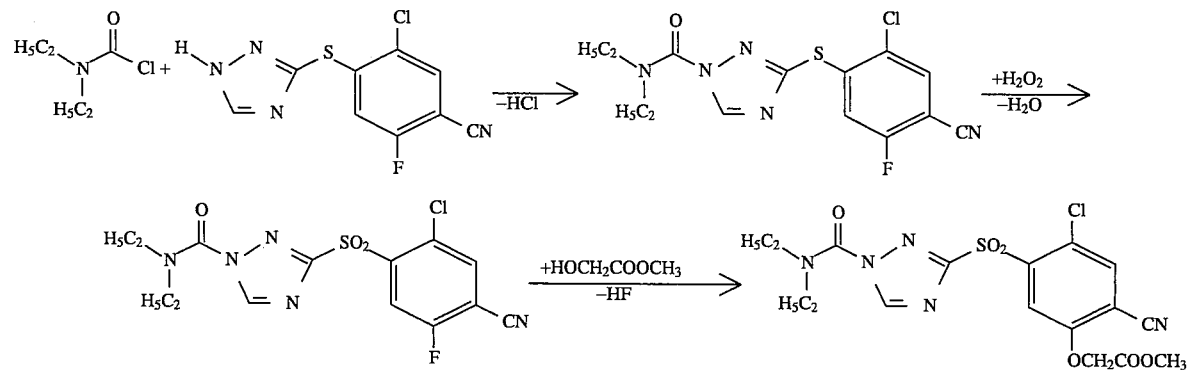

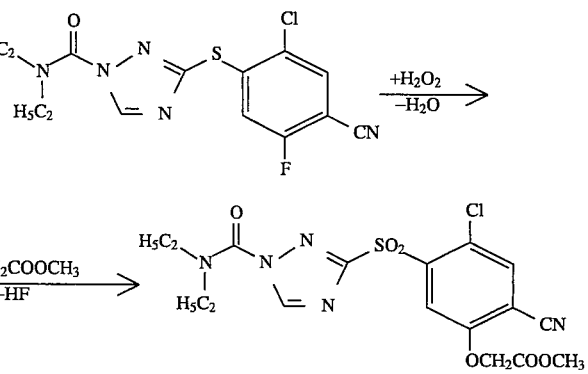

Formula (II) provides a general definition of the carbamoyl chlorides to be used as starting substances in the process according to the invention for the preparation of the compounds of the general formula (I). In formula (II), $R^1$ and $R^2$ preferably, or in particular, have those meanings which have already been given above in connection with the description of the compounds of the formula (I) as being preferred, or particularly preferred, for $R^1$ and $R^2$.

The starting substances of the formula (II) are known chemicals for organic synthesis.

Formula (III) provides a general definition of the substituted triazoles furthermore to be used as starting substances in the process according to the invention. In formula (III), m, n and X preferably, or in particular, have those meanings which have already been given above in connection with the description of the compounds of the formula (I) as being preferred, or particularly preferred, for m, n and X.

The starting substances of the formula (III) were hitherto unknown from the literature; as new substances, they are part of the present application.

The new substituted triazoles of the general formula (III) are obtained when the mercaptotriazole of the formula (V)

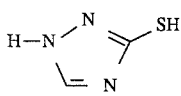

is reacted with cyanoaryl compounds of the general formula (VI)

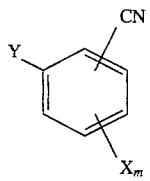

in which m and X have the abovementioned meaning and

Y represents halogen, preferably fluorine or chlorine, at temperatures between 0° C. and 100° C., if appropriate in the presence of an acid acceptor such as, for example, sodium methanolate and, if appropriate, in the presence of a diluent, such as, for example, methanol, and the product is worked up by customary methods (cf. the preparation examples).

The starting substances of the formulae (V) and (VI) are known chemicals for organic synthesis.

The process according to the invention for the preparation of the substituted carbamoyltriazoles of the formula (I) is preferably carried out in the presence of an acid acceptor. Suitable acid acceptors are the customary inorganic or organic bases or acid-binding agents. These include, for example, the hydrides, hydroxides, amides, alcoholates, acetates, carbonates or hydrogen carbonates of alkali metals or alkaline earth metals, such as, for example, sodium hydride, sodium amide, sodium methylate, sodium ethylate, potassium tert-butylate, sodium hydroxide, potassium hydroxide, ammonium hydroxide, sodium acetate, potassium acetate, calcium acetate, ammonium acetate, sodium carbonate, potassium carbonate, potassium hydrogen carbonate, sodium hydrogen carbonate or ammonium carbonate, and basic organic nitrogen compounds, such as trimethylamine, triethylamine, tributylamine, N,N-dimethylaniline, N,N-dimethyl-benzylamine, pyridine, methylpyridine, N-methylpiperidine, N,N-dimethylaminopyridine, diazabicyclooctane (DABCO), diazabicyclononene (DBN) or diazabicycloundecene (DBU).

Suitable diluents for carrying out the process according to the invention are, mainly, inert organic solvents. These include, in particular, aliphatic, alicyclic or aromatic, optionally halogenated hydrocarbons, such as, for example, benzine, benzene, toluene, xylene, chlorobenzene, dichlorobenzene, petroleum ether, hexane, cyclohexane, dichloromethane, chloroform, tetrachloromethane; ethers, such as diethyl ether, diisopropyl ether, dioxane, tetrahydrofuran, ethylene glycol dimethyl ether or ethylene glycol diethyl ether; ketones, such as acetone, butanone or methyl isobutyl ketone; nitriles, such as acetonitrile, propionitrile or benzonitrile; amides, such as N,N-dimethylformamide, N,N-dimethylacetamide, N-methylformanilide, N-methylpyrrolidone or hexamethylphosphoric triamide; esters, such as methyl acetate or ethyl acetate, sulphoxides, such as dimethyl sulphoxide, alcohols, such as methanol, ethanol, n- or i-propanol, ethylene glycol monomethyl ether, ethylene glycol monoethyl ether, diethylene glycol monomethyl ether, diethylene glycol monoethyl ether, their mixtures with water, or pure water.

Some of the abovementioned nitrogen bases, such as, for example, pyridine, can also be employed in excess and act as the diluent.

Examples of suitable oxidants for the oxidation reaction to be carried out, if appropriate, as a subsequent step are oxygen, ozone, hydrogen peroxide, chlorine, sodium hypochlorite solution, potassium permanganate, performic acid, peracetic acid, perpropionic acid and optionally halogenated perbenzoic acids.

When carrying out the process according to the invention, the reaction temperatures can be varied within a relatively wide range. In general, the process is carried out at temperatures between 0° C. and 100° C., preferably at temperatures between 10° C. and 80° C.

In general, the process according to the invention is carried out under atmospheric pressure. However, it is also possible to carry out the process at elevated or reduced pressure, in general between 0.1 bar and 10 bar.

For carrying out the process according to the invention, the starting substances required in each case are generally employed in approximately equimolar amounts. However, it is also possible to use a larger excess of one of the two components employed in each case. In general, the reactions are carried out in a suitable diluent in the presence of an acid acceptor, and the reaction mixture is stirred for several hours at the temperature required in each case. Working-up in the process according to the invention is carried out in each case by customary methods (cf. the preparation examples)

The active compounds according to the invention can be used as defoliants, desiccants, agents for destroying broad-leaved plants and, especially, as weed-killers. By weeds, in the broadest sense, there are to be understood all plants which grow in locations where they are undesired. Whether the substances according to the invention act as total or selective herbicides depends essentially on the amount used.

The active compounds according to the invention can be used, for example, in connection with the following plants:

Dicotyledon weeds of the genera:

Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver, Centaurea, Trifolium, Ranunculus and Taraxacum.

Dicotyledon cultures of the genera:

Gossypium, Glycine, Beta, Daucus, Phaseolus, Pisum, Solanum, Linum, Ipomoea, Vicia, Nicotiana, Lycopersicon, Arachis, Brassica, Lactuca, Cucumis and Cucurbita.

Monocotyledon weeds of the genera:

Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrostis, Alopecurus and Apera.

Monocotyledon cultures of the genera:

Oryza, Zea, Triticum, Hordeum, Avena, Secale, Sorghum, Panicum, Saccharum, Ananas, Asparagus and Allium.

However, the use of the active compounds according to the invention is in no way restricted to these genera, but also extends in the same manner to other plants.

The compounds are suitable, depending on the concentration, for the total combating of weeds, for example on industrial terrain and rail tracks, and on paths and squares with or without tree plantings. Equally, the compounds can be employed for combating weeds in perennial cultures, for example afforestations, decorative tree plantings, orchards, vineyards, citrus groves, nut orchards, banana plantations, coffee plantations, tea plantations, rubber plantations, oil palm plantations, cocoa plantations, soft fruit plantings and hopfields, in lawns, turf and pasture-land, and for the selective combating of weeds in annual cultures.

The compounds of the formula (I) according to the invention are particularly suitable for selectively combating monocotyledon and dicotyledon weeds in monocotyledon and dicotyledon cultures, such as cereals, beet, soya beans and cotton, both by the pre- and the post-emergence method.

The active compounds can be converted into the customary formulations, such as solutions, emulsions, wettable powders, suspensions, powders, dusting agents, pastes, soluble powders, granules, suspension-emulsion concentrates, natural and synthetic materials impregnated with active compound, and very fine capsules in polymeric substances.

These formulations are produced in a known manner, for example by mixing the active compounds with extenders, that is liquid solvents and/or solid carriers, optionally with the use of surface-active agents, that is emulsifying agents and/or dispersing agents and/or foam-forming agents.

In the case of the use of water as an extender, organic solvents can, for example, also be used as auxiliary solvents. As liquid solvents, there are suitable in the main: aromatics, such as xylene, toluene or alkylnaphthalenes, chlorinated aromatics and chlorinated aliphatic hydrocarbons, such as chlorobenzenes, chloroethylenes or methylene chloride, aliphatic hydrocarbons, such as cyclohexane or paraffins, for example petroleum fractions, mineral and vegetable oils, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, as well as water.

As solid carriers there are suitable: for example ammonium salts and ground natural minerals, such as kaolins, clays, talc, chalk, quartz, attapulgite, montmorillonite or diatomaceous earth, and ground synthetic minerals, such as highly disperse silica, alumina and silicates, as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks; as emulsifying and/or foam-forming agents there are suitable: for example nonionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates as well as albumen hydrolysis products; as dispersing agents there are suitable: for example lignin-sulphite waste liquors and methylcellulose.

Adhesives such as carboxymethylcellulose and natural and synthetic polymers in the form of powders, granules or latexes, such as gum arabic, polyvinyl alcohol and polyvinyl acetate, as well as natural phospholipids, such as cephalins and lecithins, and synthetic phospholipids, can be used in the formulations. Further additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 per cent by weight of active compound, preferably between 0.5 and 90%.

For combating weeds, the active compounds according to the invention, as such or in the form of their formulations, can also be used as mixtures with known herbicides, finished formulations or tank mixes being possible.

Suitable herbicides for the mixtures are known herbicides, for example anilides such as, for example, diflufenican and propanil; arylcarboxylic acids such as, for example, dichloropicolinic acid, dicamba and picloram; aryloxyalkanoic acids such as, for example, 2,4 D, 2,4 DB, 2,4 DP, fluroxypry, MCPA, MCPP and triclopyr; aryloxy-phenoxy-alkanoic esters such as, for example, diclofop-methyl, fenoxaprop-ethyl, fluazifop-butyl, haloxyfop-methyl and quizalofop-ethyl; azinones such as, for example, chloridazon and norflurazon; carbamates such as, for example, chlorpropham, desmedipham, phenmediphamand propham; chloroacetanilides such as, for example, alachlor, acetochlor, butachlor, metazachlor, metolachlor, pretilachlor and propachlor; dinitroanilines such as, for example, oryzalin, pendimethalin and trifluralin; diphenyl ethers such as, for example, acifluorfen, bifenox, fluoroglycofen, fomesafen, halosafen, lactofen and oxyfluorfen; ureas such as, for example, chlortoluron, diuron, fluometuron, isoproturon, linuron and methabenzthiazuron; hydroxylamines such as, for example, alloxydim, clethodim, cycloxydim, sethoxydim and tralkoxydim; imidazolinones such as, for example, imazethapyr, imazamethabenz, imazapyr and imazaquin; nitriles such as, for example, bromoxynil, dichlobenil and ioxynil; oxyacetamides such as, for example, mefenacet; sulphonylureas such as, for example, amidosulfuron, bensulfuron-methyl, chlorimuron-ethyl, chlorsulfuron, cinosulfuron, metsulfuron-methyl, nicosulfuron, primisulfuron, pyrazosulfuron-ethyl, thifensulfuron-methyl, triasulfuron and tribenuron-methyl; thiocarbamates such as, for example, butylate, cycloate, di-allate, EPTC, esprocarb, molinate, prosulfocarb, thiobencarb and tri-allate; triazines such as, for example, atrazine, cyanazine, simazine, simetryne, terbutryne and terbutylazine; triazinones such as, for example, hexazinone, metamitron and metribuzin; others such as, for example, aminotriazole, benfuresate, bentazone, cinmethylin, clomazone, clopyralid, difenzoquat, dithiopyr, ethofumesate, fluorochloridone, glufosinate, glyphosate, isoxaben, pyridate, quinchlorac, quinmerac, sulphosate and tridiphane.

Mixtures with other known active compounds, such as fungicides, insecticides, acaricides, nematicides, bird repellants, plant nutrients and agents which improve soil structure, are also possible.

The active compounds can be used as such, in the form of their formulations or in the use forms prepared therefrom by further dilution, such as ready-to-use solutions, suspensions, emulsions, powders, pastes and granules. They are used in the customary manner, for example by watering, spraying, atomizing or scattering.

The active compounds according to the invention can be applied either before or after emergence of the plants. They can also be incorporated into the soil before sowing.

The amount of active compound used can vary within a relatively wide range. It depends essentially on the nature of the desired effect. In general, the amounts used are between 10 g and 10 kg of active compound per hectare of soil surface, preferably between 50 g and 5 kg per ha.

The preparation and use of the active compounds according to the invention can be seen from the following examples.

PREPARATION EXAMPLES

EXAMPLE 1

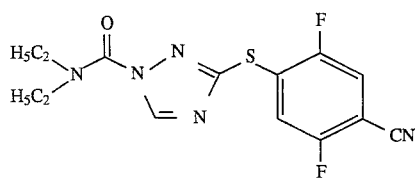

A mixture of 3.5 g (14.7 mmol) of 3-(4-cyano-2,5-difluoro-phenylthio)-1H-1,2,4-triazole, 2.1 g (15.3 mmol) of N,N-diethyl-carbamoyl chloride and 20 ml of pyridine is stirred for 3 days at 20° C. It is then diluted with water to approximately twice its volume, filtered and washed in succession with 1N hydrochloric acid and with water.

5.5 g (91.5% of theory) of 3-(4-cyano-2,5-difluoro-phenylthio)-1-diethylaminocarbonyl-1H- 1,2,4-triazole of melting point 80° C. are obtained.

EXAMPLE 2

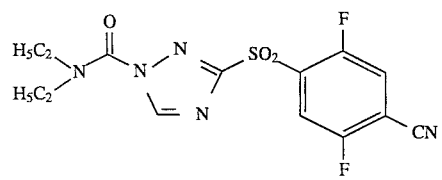

A mixture of 4.0 g (10 mmol) of 3-(4-cyano-2,5-difluoro-phenylthio)-1-diethylaminocarbonyl-1 H-1,2,4-triazole, 4.6 g (22 mmol) of 3-chloro-perbenzoic acid (80% strength) and 75 ml of chloroform is first stirred for 30 minutes at 0° C. and then for 15 hours at 20° C. After a further 0.9 g (4.5 mmol) of 3-chloro-perbenzoic acid has been added, the mixture is stirred for a further 15 hours at 20° C. It is then shaken three times with saturated sodium carbonate solution and the organic phase is concentrated in vacuo. The residue is taken up in ethyl acetate, and the product is precipitated by adding hexane and isolated by filtration.

1.2 g (32.54 of theory) of 3-(4-cyano-2,5-difluoro-phenylsulphonyl)-1-diethylaminocarbonyl-1H- 1,2,4-triazole of melting point 98° C. are obtained.

Other examples of the compounds of the formula (I) which can be prepared analogously to Examples 1 and 2 and following the general description of the preparation process according to the invention are those listed in Table 1 below.

TABLE 1

Examples of the compounds of the formula (I)

| Ex. No. | m | n | $R^1$ | $R^2$ | Position of CN | (Position-) X | Melting Point (°C.) |
|---|---|---|---|---|---|---|---|
| 3 | 2 | 0 | $CH_3$ | $CH_3$ | 4 | (2,5-)F | 59 |
| 4 | 2 | 0 | $C_2H_5$ | $C_2H_5$ | 4 | (2-)Cl, (5-)F | |
| 5 | 2 | 1 | $C_2H_5$ | $C_2H_5$ | 4 | (2-)Cl, (5-)F | |
| 6 | 2 | 2 | $C_2H_5$ | $C_2H_5$ | 4 | (2-)Cl, (5-)F | |
| 7 | 0 | 0 | $C_2H_5$ | $C_2H_5$ | 4 | — | |
| 8 | 0 | 1 | $C_2H_5$ | $C_2H_5$ | 4 | — | |
| 9 | 0 | 2 | $C_2H_5$ | $C_2H_5$ | 4 | — | |
| 10 | 2 | 2 | $CH_3$ | $CH_3$ | 4 | (2, 5-) $SCH_3$ | |
| 11 | 2 | 2 | $CH_3$ | $CH_3$ | 4 | (2, 5-) $OCH_3$ | |
| 12 | 2 | 2 | $C_2H_5$ | $C_2H_5$ | 4 | (2-) Cl, (5-) $NH_2$ | |
| 13 | 2 | 2 | $C_2H_5$ | $C_2H_5$ | 4 | (2-)Cl, (5-) $NHSO_2CH_3$ | |
| 14 | 1 | 2 | $C_2H_5$ | $C_2H_5$ | 4 | (2-)F | |
| 15 | 1 | 2 | $C_2H_5$ | $C_2H_5$ | 4 | (2-)$OCH_3$ | |
| 16 | 1 | 2 | $CH_3$ | $CH_3$ | 4 | (2-)$SC_2H_5$ | |
| 17 | 1 | 2 | $CH_3$ | $CH_3$ | 4 | (3-)F | |
| 18 | 1 | 2 | $C_2H_5$ | $C_2H_5$ | 4 | (3-)F | |
| 19 | 1 | 2 | $C_3H_7$ | $C_3H_7$ | 4 | (3-)F | |
| 20 | 1 | 2 | $C_2H_5$ | $C_2H_5$ | 4 | (3-)$NHSO_2C_2H_5$ | |
| 21 | 1 | 2 | $-(CH_2)_6-$ | | 4 | (3-)F | |
| 22 | 1 | 2 | $-(CH_2)_5-$ | | 4 | (3-)F | |
| 23 | 1 | 2 | $-(CH_2)_4-$ | | 4 | (3-)F | |
| 24 | 2 | 2 | $-(CH_2)_5-$ | | 4 | (2,5-)F | |
| 25 | 2 | 0 | $C_2H_5$ | $C_2H_5$ | 4 | (2-)F, (5-)Cl | 107 |
| 26 | 2 | 1 | $C_2H_5$ | $C_2H_5$ | 4 | (2-)F, (5-)Cl | 140 |
| 27 | 2 | 2 | $C_2H_5$ | $C_2H_5$ | 4 | (2-)F, (5-)Cl | |
| 28 | 1 | 2 | $C_2H_5$ | $CH_3$ | 4 | 2-Cl | |
| 29 | 4 | 0 | $C_2H_5$ | $C_2H_5$ | 4 | (2,3,5,6-)F | 52 |
| 30 | 4 | 1 | $C_2H_5$ | $C_2H_5$ | 4 | (2,3,5,6-)F | |
| 31 | 4 | 2 | $C_2H_5$ | $C_2H_5$ | 4 | (2,3,5,6-)F | 32 |

Starting substance of the formula (III): Example (III-1)

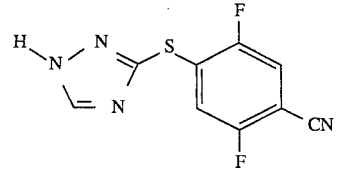

A mixture of 5.3 g (52 mmol) of 3-mercapto-1H-1,2,4-triazole, 8.2 g (52 mmol) of 2,4,5-trifluoro-benzonitrile, 2.8 g (52 mmol) of sodium methanolate and 50 ml of methanol is stirred for 15 hours at 20° C. and then for a further 12 hours at 60° C. and for 8 hours under reflux. After the mixture has been concentrated to approximately half its volume and cooled, the product which has precipitated in crystalline form is isolated by filtration.

4.0 g (32% of theory) of 3-(4-cyano-2,5-difluoro-phenylthio)-1H-1,2,4-triazole of melting point 185° C. are obtained.

USE EXAMPLES

The use examples which follow, compound (A) given below was employed as comparison substance:

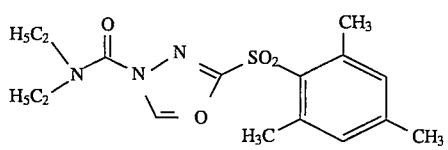

1-Diethylaminocarbonyl)-3-(2,4,6-trimethylphenyl-sulphonyl)-1,2,4-triazole (disclosed in EP-A 332 133)

EXAMPLE A

Post-emergence test

Solvent: 5 parts by weight of acetone

Emulsifier: 1 part by weight of alkylaryl polyglycol ether

To produce a suitable preparation of active compound, 1 part by weight of active compound is mixed with the stated amount of solvent, the stated amount of emulsifier is added and the concentrate is diluted with water to the desired concentration.

In the field, plots with test plants which had a height of approximately 3–10 cm were sprayed with an amount of the preparation of active compound such that the plants were wetted uniformly. The decisive factor is the application rate of the active compound per unit area. After three weeks, the degree of damage to the plants is rated in % damage in comparison to the untreated control. The figures denote:

0%=no action (like untreated control)

100%=total destruction

In this test, a powerful activity against weeds such as, for example, Galium (80%), Ipomoea (90%), Alopecurus (50%) and Cyperus (50%) was shown, for example, by the compounds of Preparation Examples 1 and 2 at an application rate of 1000 g/ha, while the tolerance by crop plants such as, for example, beet and cotton, was very good (0%).

EXAMPLE B

Pre-emergence test

Solvent: 5 parts by weight of acetone

Emulsifier: 1 part by weight of alkylaryl polyglycol ether

To produce a suitable preparation of active compound, 1 part by weight of active compound is mixed with the stated amount of solvent, the stated amount of emulsifier is added and the concentrate is diluted with water to the desired concentration.

Seeds of the test plants are sown in normal soil and, after 24 hours, the soil was watered with the preparation of the active compound. It is expedient to keep constant the amount of water per unit area. The concentration of the active compound in the preparation is of no importance, only the amount of active compound applied per unit area being decisive. After three weeks, the degree of damage to the plants is rated in % damage in comparison to the development of the untreated control. The figures denote:

0%=no action (like untreated control)

100%=total destruction

In this test, a powerful activity against weeds such as, for example, Alopecerus (95%) Lolium (80–95%) Galinsoga (80–100%), Abutilon (95%) and Poa (100%) was shown, for example, by the compounds of Preparation Examples 1 and 2 at application rates of 500 g/ha, while the tolerance by crop plants such as, for example, barley and soya beans, was very good (0%).

It will be understood that the specification and examples are illustrative but not limitative of the present invention and that other embodiments within the spirit and scope of the invention will suggest themselves to those skilled in the art.

What is claimed is:

1. A substituted carbamoyltriazole of the formula

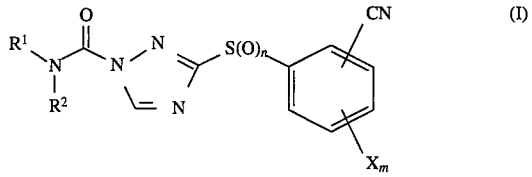

wherein m represents the numbers 0, 1, 2, 3 or 4, n represents the numbers 0, 1 or 2, $R^1$ represents a radical from the group consisting of alkyl, alkenyl or alkinyl, each of which has up to 6 carbon atoms and each of which is optionally substituted by halogen, $R^2$ represents a radical from the group consisting of alkyl, alkenyl or alkinyl, each of which has up to 6 carbon atoms and each of which is optionally substituted by halogen, or together with $R^1$ represents alkanediyl having 2 to 6 carbon atoms, and X represents halogen, hydroxyl, amino, mercapto, X furthermore represents a radical from the group consisting of alkyl, alkoxy, alkylthio, alkylamino, alkanoylamino or alkylsulphonylamino, each of which has up to 6 carbon atoms in the alkyl groups and each of which is optionally substituted by halogen, cyano, hydroxyl, carboxyl, $C_1$–$C_4$-alkoxy, $C_1$–$C_4$-alkyl-carbonyl or $C_1$–$C_4$-alkoxy-carbonyl, X furthermore represents a radical from the group consisting of cycloalkyloxy, cycloalkylthio, cycloalkylamino, cycloalkylalkoxy, cycloalkyl-alkylthio or cycloalkyl-alkylamino, each of which has 3 to 6 carbon atoms in the cycloalkyl groups and, when present, 1 to 4 carbon atoms in the alkyl groups and each of which is optionally substituted by halogen, cyano, carboxyl, $C_1$–$C_4$-alkyl or $C_1$–$C_4$-alkoxy-carbonyl, or X furthermore represents a radical from the group consisting of aryloxy, arylthio, arylamino, arylcarbonyl, arylsulphonyl, arylalkyl, arylalkoxy, arylalkylthio, arylalkylamino, arylalkylcarbonyl or arylalkylsulphonyl, each of which has 6 to 10 carbon atoms in the aryl groups and, when present, 1 to 4 carbon atoms in the alkyl groups, and each of which is optionally substituted by halogen, cyano, nitro, hydroxyl, amino, carboxyl, $C_1$–$C_4$-alkyl, $C_1$–$C_4$-halogenoalkyl, $C_1$–$C_4$-alkoxy, $C_1$–$C_4$-halogenoalkoxy, $C_1$–$C_4$-alkylthio, $C_1$–$C_4$-halogenoalkylthio, $C_1$–$C_4$-alkylsulphinyl, $C_1$–$C_4$-halogenoalkylsulphinyl, $C_1$–$C_4$-alkylsulphonyl, $C_1$–$C_4$-halogenoalkylsulphonyl or $C_1$–$C_4$-alkoxycarbonyl.

2. A substituted carbamoyltriazole according to claim 1, wherein m represents the numbers 0, 1, 2, 3 or 4, n represents the numbers 0, 1 or 2, $R^1$ represents a radical from the group consisting of methyl, ethyl, n- or i-propyl, n-, i- or s-butyl, propenyl, butenyl, propinyl or butinyl, each of which is optionally substituted by fluorine, $R^2$ represents a radical from the group consisting of methyl, ethyl, n-or i-propyl, n-, i- or s-butyl, propenyl, butenyl, propinyl or butinyl, each of which is optionally substituted by fluorine, or together with $R^1$ represents ethane-1,2-diyl (dimethylene), propane-1,3-diyl (trimethylene) or butane-1,4-diyl (tetramethylene) and X represents fluorine, chlorine, bromine, hydroxyl, amino, mercapto, X furthermore represents a radical from the group consisting of methyl, ethyl, n- or i-propyl, n-, i-, s-, or t-butyl, methoxy, ethoxy, n- or i-propoxy, n-, i-, s- or t-butoxy, methylthio, ethylthio, n- or i -propylthio, n-, s -, i - or t -butylthio, methylamino, ethylamino, n- or i -propylamino, n-, i-, s- or t-butylamino, acetylamino, propionylamino, butyroylamino, methylsulphonylamino, ethylsulphonylamino, n- or i-propylsulphonylamino, n-, i-, s- or t-butylsulphonylamino, each of which is optionally substituted by fluorine, chlorine, bromine, cyano, hydroxyl, carboxyl, methoxy, ethoxy, methoxycarbonyl or ethoxycarbonyl, X furthermore represents a radical from the group consisting of cyclopentyloxy, cyclohexyloxy, cylcopentylthio, cyclohexylthio, cyclopentylamino, cyclohexylamino, cyclopentylmethoxy, cyclohexylmethoxy, cyclopentyl-methylthio, cyclohexylmethylthio, cyclopentylmethylamino, or cyclohexyl-methylamino, each of which is optionally substituted by fluorine, chlorine, bromine, cyano, carboxyl, methyl, ethyl, n- or i-propyl, methoxycarbonyl or ethoxy-carbonyl, or X further represents a radical from the group consisting of phenoxy, phenylthio, phenylamino, phenylcarbonyl, phenylsulphonyl, benzyl, benzyloxy, benzylthio, benzylamino, phenylacetyl or benzylsulphonyl, each of which is optionally substituted by fluorine, chlorine, bromine, cyano, nitro, hydroxyl, amino, carboxyl, methyl, ethyl, trifluoromethyl, methoxy, ethoxy, difluoromethoxy, trifluoromethoxy, methylthio, ethylthio, difluoromethylthio, trifluoromethylthio, methylsulphinyl, ethylsulphinyl, methylsulphonyl, ethylsulphonyl, trifluoromethylsulphonyl, methoxycarbonyl or ethoxycarbonyl.

3. A compound according to claim 1, wherein such compound is 3-(4-cyano-2,5-difluorophenylthio)-1-diethylaminocarbonyl-1H-1,2,4-triazole of the formula

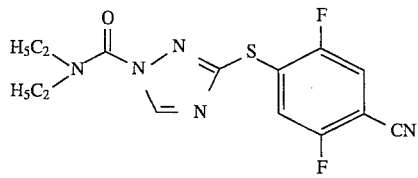

4. A compound according to claim 1, wherein such compound is 3-(4-cyano-2,5-difluorophenylsulphonyl)-1-diethylaminocarbonyl-1H-1,2,4-triazole of the formula

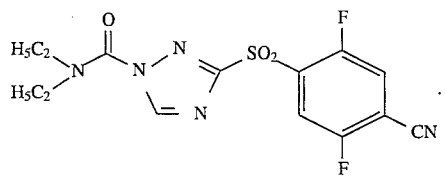

5. A herbicidal composition comprising a herbicidally effective amount of a compound according to claim 1 and a diluent.

6. A method of combating unwanted vegetation which comprises administering to such vegetation as to a locus from which it is desired to exclude such vegetation a herbicidally effective amount of a compound according to claim 1.

7. The method according to claim 6, wherein such compound is 3-(4-cyano-2,5-difluorophenylthio)-1-diethylaminocarbonyl-1H-1,2,4-triazole, and 3-(4-cyano-2,5-difluorophenylsulphonyl)-1-diethylaminocarbonyl-1H-1,2,4-triazole.

* * * * *